US00PP35035P2

(12) United States Plant Patent
Hansen

(10) Patent No.: US PP35,035 P2
(45) Date of Patent: Mar. 14, 2023

(54) ***VERONICA* PLANT NAMED 'EVER AFTER'**

(50) Latin Name: *Veronica spicata*
Varietal Denomination: Ever After

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/803,458

(22) Filed: Jul. 20, 2022

(51) Int. Cl.
*A01H 5/02* (2018.01)
*A01H 6/68* (2018.01)

(52) U.S. Cl.
USPC ..... Plt./251
CPC ..... *A01H 6/68* (2018.05)

(58) Field of Classification Search
USPC ..... Plt./251
CPC ..... A01H 5/02
See application file for complete search history.

*Primary Examiner* — Kent L Bell

(57) ABSTRACT

The new and distinct cultivar of ornamental Spiked Speedwell, *Veronica spicata* plant named 'Ever After', with medium height, stiff, upright, compound branched spikes of densely-arranged lilac-colored flowers beginning in early summer and continuing for twelve to fourteen weeks above dark-green, lanceolate, highly lustrous foliage. The new plant is useful in the landscape as a specimen, en masse, as a container plant, or as a cut flower, and maintains its foliage through the season with good disease tolerance, specifically rust resistance.

2 Drawing Sheets

Botanical classification: *Veronica spicata.*
Variety denomination: 'Ever After'.

STATEMENT REGARDING PRIOR DISCLOSURES UNDER 37 CFR 1.77(b)(6)

The claimed plant was featured in the form of a photograph and brief description on a website operated by Walters Gardens, Inc. on Dec. 1, 2021. Subsequently, on Jun. 8, 2022 the new plant was described with a photograph in the "Walters Gardens 2022-2023 Catalog" by Walters Gardens, Inc. The first sale of *Veronica* 'Ever After' was on Aug. 2, 2021 to Corso's Flower & Garden by Walters Gardens, Inc., who obtained the plant and all information relating thereto, from the inventor. No plants of *Veronica* 'Ever After' have been sold in this country or anywhere in the world, nor has any disclosure of the new plant been made, more than one year prior to the filing date of this application, and such sale or disclosure within one year was either derived directly or indirectly from the inventor and would be a 35 U.S.C § 102b exception.

BACKGROUND OF THE INVENTION

The present invention relates to the new and distinct cultivar of Spiked Speedwell, botanically known as *Veronica* 'Ever After', and hereinafter referred to as the cultivar 'Ever After' or the "new plant". The new plant was a self-pollination by the inventor on May 15, 2015, in the hybridizing greenhouses of a wholesale perennial nursery in Zeeland, Mich., USA. The parent was a proprietary unreleased hybrid known only by the breeder code 14-1-1 (not patented).

The new plant was assigned the breeder code of 15-3-1. 'Ever After' has been asexually propagated initially by division and later by basal cuttings and shoot tip tissue culture at the same nursery in the greenhouses in Zeeland, Mich., since the summer of 2017 with subsequent asexually propagated plants found to be identical to the original selection with all the same traits as the original seedling.

BRIEF SUMMARY OF THE PLANT

*Veronica* 'Ever After' is unique from all other Spiked Speedwell known to the inventor. Several other cultivars may have some similar traits, but this is the only variety known by the inventor to have the following characteristic combinations that establish the new plant as unique:

1. Medium height with stiff, upright spikes above dense stems of dark-green foliage;
2. Flowering in long spikes;
3. Scapes with numerous, dense flowers of lilac-colored petals;
4. Dark-green, highly lustrous, lanceolate foliage;
5. Compound-branched peduncles begin blooming in early summer and continue for twelve to fourteen weeks into early autumn;
6. Maintains foliage through the season with good disease resistance.

The closest comparison varieties known to the inventor are 'Mona Lisa Smile' U.S. Plant Pat. No. 30,477, 'Atomic Lilac' U.S. Plant Pat. No. 21,867, 'Hocus Pocus' U.S. Plant Pat. No. 23,853, 'Blue Skywalker' U.S. Plant Pat. No. 29,406, 'Princess Leia' U.S. Plant Pat. No. 34,278, and 'Amethyst Plume' U.S. Plant Pat. No. 24,411.

'Mona Lisa Smile' is taller in habit and has a flower color that is a lighter rosy purple. 'Atomic Lilac' has a slightly taller habit, narrower width and the foliage is broader and more ovate-shaped, the flowers are on slightly shorter peduncles. 'Hocus Pocus' has a shorter habit, and the flowers are a vivid violet-purple. 'Blue Skywalker' is taller, has a shorter flowering season, and the flowers are a different hue. 'Princess Leia' is taller, with a shorter flowering season, and the flowers are rosy-purple. 'Amethyst Plume' has flowers that are deep purple-pink with peduncles that are more branched near the apex, and the habit is much taller than the new plant.

The new plant can also be compared with cultivars in the ancestry. 'Sweet Lullaby' U.S. Plant Pat. No. 23,611 has a much shorter habit and the flowers are pure baby pink. 'Purpleicious' U.S. Plant Pat. No. 17,639 has a narrower and slightly short habit with fewer stems per plant, the foliage is a lighter green, and the flower color is a more reddish, purple.

The parent, 14-1-1, has flowers that are more pinkish on taller sterns and the habit was more open and not as sturdy.

BRIEF DESCRIPTION OF THE DRAWINGS

The photographs of the new plant demonstrate the overall appearance and unique traits of 'Ever After' as a two-year-old plant grown in a full-sun display garden in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
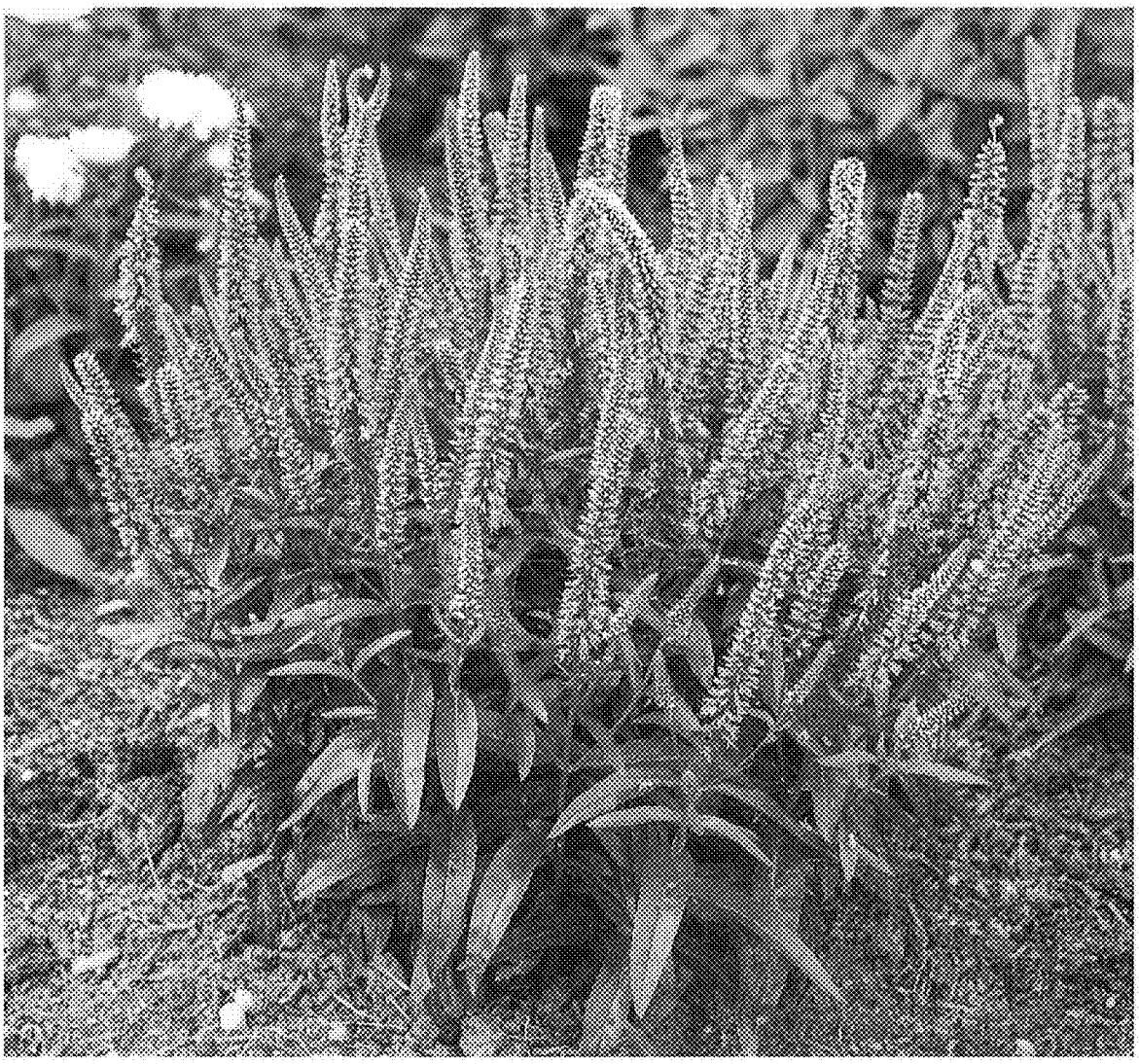
FIG. 1 shows the habit of the new plant in early full flower.
Figure 2:
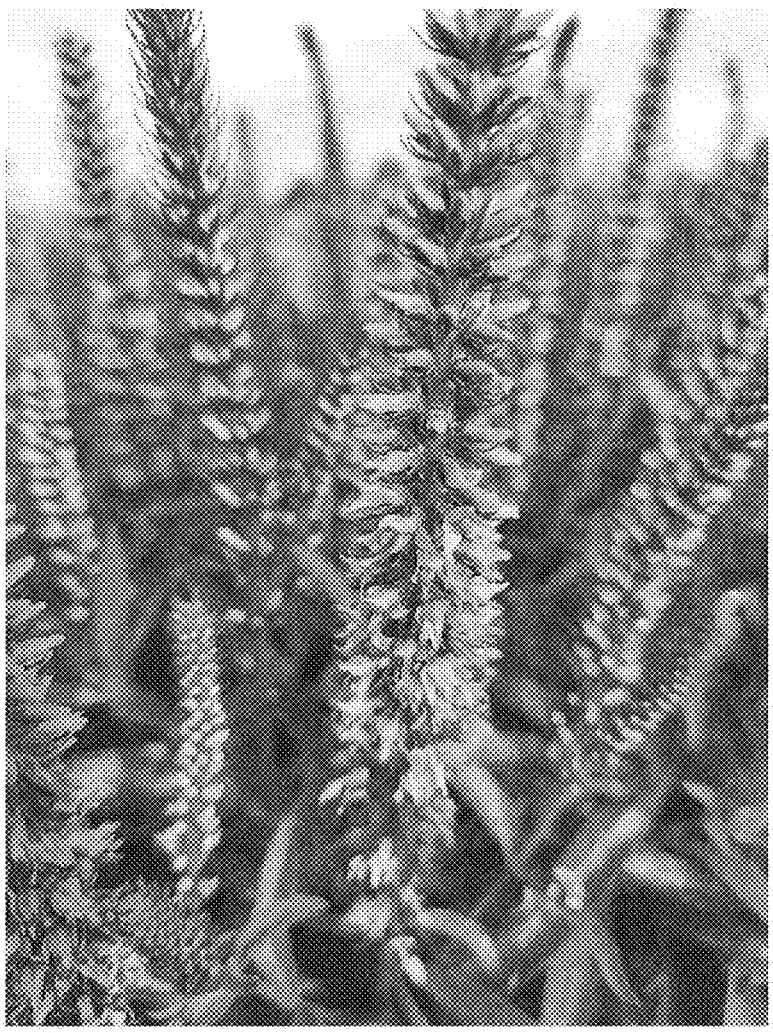
FIG. 2 shows a close-up of the flowers and buds.

The following descriptions and color references of *Veronica* 'Ever After' are based on the 2015 edition of The Royal Horticultural Society Colour Chart except where common dictionary terms are used. 'Ever After' has not been observed under all possible environments. The phenotype may vary slightly with different growing environments such as temperature, light, fertility, soil pH, moisture and maturity levels, but without any change in the genotype. The following observations and descriptions are based on two-year-old plants grown in a full-sun display garden of a wholesale perennial nursery in Zeeland, Mich.

Botanical classification: *Veronica spicata.*

Parentage: The parent is the proprietary unreleased hybrid 14-1-1 comprising ancestry from 'Sweet Lullaby', 'Purpleicious' and an unreleased proprietary hybrid code 13-32-1 (not patented).

Propagation: The plant roots from cuttings in about 2 weeks and finishes to flowering in a 3.8-liter container in 8 to 10 weeks following an optimal vernalization period of about 8 weeks.

Roots: Fibrous; heavily branching; color between RHS 164C and RHS 164D.

Plant habit: Hardy herbaceous perennial, compact, with about 50 stems; main stems branching in distal portion; to about 66 cm tall and clumping to about 60 cm wide; flowering beginning early summer in Michigan and continuing for 12 to 14 weeks.

Leaves: Simple; flat; lanceolate; opposite; margin serrulate, serrated with about 5 teeth per centimeter; adaxial micro-puberulent and glabrous abaxial, highly lustrous adaxial and matte abaxial; acute apex; distal leaves with attenuate base and proximal leaves with rounded to cuneate base; about 90 mm long by 67 mm wide near the middle, average about 75 mm long and 23 mm wide, decreasing in both length and width distally; about 16 leaves per stem.

Leaf color: Mature adaxial nearest RHS 139A, abaxial nearest RHS 146A; young expanding adaxial nearest RHS 137A, abaxial nearest RHS 137B.

Veins: Pinnate, adaxial midrib costate; glabrous adaxial, abaxial midrib sparsely puberulent and glabrate, secondary abaxial veins glabrous.

Vein color: Adaxial midrib and proximal lateral veins nearest RHS 148C and distal lateral veins nearest RHS 139A; abaxial midrib nearest RHS 148C distally and nearest RHS 146C proximally and lateral veins nearest RHS 137B.

Petiole: Simple, puberulent abaxial and glabrous adaxial; margin micro-ciliolate; base slightly clasping; to about 10 mm long and 4 mm wide decreasing distally to an average about 6.5 mm long and 3 mm wide.

Petiole color: Adaxial between RHS 138B and RHS 146C; abaxial nearest RHS 138A.

Stem: Cylindrical; puberulent; length about 20 to 26 cm before flowers, diameter about 5 mm at base; color nearest RHS 146D.

Internodes: Typically 8 below flowers; average about 2.5 cm apart; node color variable, nearest RI-IS 138A.

Inflorescence: Compound branched upright spikes in compressed conglomerate; about 30 to 40 cm long and 10 cm to 14 cm wide with two lateral branches, each with two branches; the plant continues to flower adding to the terminal end of the main stem and branches, with about 400 flowers per center stem, 150 flowers per primary branch and about 800 to 1000 flowers per branched peduncle.

Flower bud one to two days prior to opening: Convolute, oblong; rounded base and acute apex; glabrous; about 8 mm long and 2 mm diameter.

Flower bud color one to two days prior to opening: Between RHS 85A and RHS N82D.

Flowers: Zygomorphic, perfect, complete; about 10 mm wide and about 9 mm long to exserted anthers; corolla about 10 mm across, 6 mm tall, and about 8 mm long; corolla tube fused in basal 3 mm, and 2 mm diameter near base; flowers persist individually for 4 to 6 days whether on the plant or as cut flower; petals self-cleaning, sepals and style persistent.

Flower attitude: Outwardly.

Flower fragrance: None detectible.

Flower timing: Early summer and continuing for at least six weeks.

Petals: Four; one slightly larger dorsal petal above, two lateral, one ventral slightly smaller below; acute apices; entire; glabrous adaxial and abaxial except basal 2 mm adaxial of fused tube with pubescent tuft; fused in basal 3 mm; larger dorsal petal 3 mm wide and 7 mm long, lateral side petals about 7 mm long by 2 mm wide, ventral petal about 7 mm long and 1.5 mm wide.

Petal color: Abaxial and adaxial between RHS 91B and RHS 91A with corolla tube base lightening RHS NN155D with proximal 0.5 mm nearest RHS 145D; adaxial tuft of hairs nearest RHS NN155D.

Androecium:

*Filaments.*—Two; divergent; cylindrical; glabrous; epipetalous about 1.0 mm from base; about 7 mm long by 0.3 mm diameter; color nearest RHS 92A distally and in the proximal one to two mm near white, RHS NN155C.

*Anther.*—Dorsifixed, longitudinal; ellipsoidal; with acute rounded becoming acute, base rounded; about 2 mm long and 1 mm wide; color nearest RHS N77C.

*Pollen.*—Abundant, globose, less than 0.1 mm; color nearest RHS 8C.

Gynoecium: One, superior; exserted; persists after petal drop; about 7 mm long.

*Style.*—Cylindrical; straight; attitude outwardly to slightly drooping; about 6 mm long by 0.3 mm; color nearest RHS 83C.

*Stigma.*—Globose; about 0.2 mm in diameter; color RHS 85C.

*Ovary.*—Ellipsoid; about 1 mm long and 0.7 mm across; color nearest RHS 145A.

Calyx: Campanulate; 4 mm long, 4 mm across and 6 mm tall.

Sepals: Four; two larger and two smaller; lanceolate; adaxial dull, glabrous; abaxial microscopically puberulent; acute apex; basal 1 mm fused and then flared forming a broad campanulate calyx; margin entire, micro-ciliolate; larger pair about 4 mm long and 1 mm wide; smaller pair about 3 mm long and 1 mm wide.

Sepal color: Abaxial and adaxial nearest RHS NN137A.

Peduncle: About 50 per plant; raceme; strong, stiff but flexible; virgate; compound branched at two upper nodes; cylindrical; puberulent distally and at branches, to glabrescent proximally; flowering portion to about 40 cm long, about 14 cm across with branches; central stern about 3 mm diameter below flowers.

Main peduncle, primary and secondary branches color: Nearest RHS 146D.

Branches: Cylindrical; puberulent; at about 30° angle from vertical and then erect in flowering portion; to about 25 cm long and 2 mm diameter.

Secondary branches: Cylindrical; puberulent; to about 7 cm long and 1 mm diameter, at about 30° angle from vertical and then erect in flowering portion.

Pedicel: Rigid; cylindrical, puberulent; about 0.5 mm long and 0.5 mm wide, attitude outwardly to slightly upwardly.

Pedicel color: Nearest RHS 138B.

Bract: Single; subtending each flower; linear; narrowly acute apex; entire; sessile truncate base; proximal bracts about 26 mm long and 3 mm wide and decreasing distally to about 3 mm long and less than 1 mm wide.

Bract color: Adaxial between RHS NN137A and RHS 139A, abaxial and nearest RHS NN137A.

Fruit: Ellipsoid with rounded apex and base, about 2.5 mm long and 2 mm across; color between RHS 165A and RHS 165B.

Growth: The new plant grows best with plenty of moisture and adequate drainage, but is able to tolerate some drought when mature.

Hardiness: Winter hardiness at least from USDA zone 4 through 8.

Disease and pest resistance beyond what is typical of that of other spike speedwell has not been observed.

I claim:

1. A new and distinct cultivar of ornamental Spiked Speedwell, *Veronica* plant named 'Ever After', as herein described and illustrated.

* * * * *